(12) United States Patent
Loose et al.

(10) Patent No.: US 8,739,637 B2
(45) Date of Patent: Jun. 3, 2014

(54) APPLICATIONS FOR REAL-TIME MASS RATIO, MASS FLOW AND PARTICLE SIZE MEASUREMENT OF PARTICLE LADEN FLOWS

(75) Inventors: Douglas H. Loose, Southington, CT (US); Daniel L. Gysling, Glastonbury, CT (US); Alex Van Der Spek, Rotterdam (NL)

(73) Assignee: CIDRA Corporate Services Inc., Wallingford, CT (US)

( * ) Notice: Subject to any disclaimer, the term of this patent is extended or adjusted under 35 U.S.C. 154(b) by 266 days.

(21) Appl. No.: 13/146,598

(22) PCT Filed: Feb. 1, 2010

(86) PCT No.: PCT/US2010/022737
§ 371 (c)(1),
(2), (4) Date: Oct. 11, 2011

(87) PCT Pub. No.: WO2010/088602
PCT Pub. Date: Aug. 5, 2010

(65) Prior Publication Data
US 2012/0017699 A1 Jan. 26, 2012

Related U.S. Application Data

(60) Provisional application No. 61/148,475, filed on Jan. 30, 2009, provisional application No. 61/153,131, filed on Feb. 17, 2009.

(51) Int. Cl.
*G01F 1/20* (2006.01)

(52) U.S. Cl.
USPC ...................................... 73/861.18

(58) Field of Classification Search
USPC ................................ 73/861.42, 861.04, 29.01
See application file for complete search history.

(56) References Cited

U.S. PATENT DOCUMENTS

| | | | |
|---|---|---|---|
| 5,714,691 A * | 2/1998 | Hill | ........................... 73/861.04 |
| 7,134,320 B2 | 11/2006 | Gysling et al. | |
| 7,165,464 B2 | 1/2007 | Gysling et al. | |
| 7,343,820 B2 | 3/2008 | Gysling et al. | |
| 7,363,800 B2 | 4/2008 | Gysling et. al. | |
| 7,367,240 B2 | 5/2008 | Gysling et al. | |
| 2007/0044572 A1 * | 3/2007 | Davis et al. | ................ 73/861.42 |

FOREIGN PATENT DOCUMENTS

CN 1217054 5/1999

OTHER PUBLICATIONS

2 Pages International Search Report.
8 Pages International Preliminary Report on Patentability.
CN1217054 English Language Abstract (1 page).

* cited by examiner

*Primary Examiner* — Jewel V Thompson

(57) ABSTRACT

Techniques are provided for monitoring particle laden flows in a pipe, that include receiving signalling containing information about a parameter related to a particle laden flow in a pipe, the parameter including either (a) a sound level propagating through the particle laden flow in the pipe, or (b) a static pressure due to an acceleration of the particle laden flow in the pipe; and determining a measurement of a particle size and either a mass flow rate, or a particle-to-air mass ratio, or both the mass flow rate and the particle-to-air mass ratio, associated with the particle laden flow, based at least partly on a change in the parameter.

42 Claims, 10 Drawing Sheets

Possible Implementation of Mass Flow and Particle Size Meter for Particle Laden Flow

System 10

A data gathering module 12 configured to respond to a particle laden flow in a pipe, and provide signaling containing information about a parameter related to the particle laden flow, the parameter including either (a) a sound level propagating through the particle laden flow in the pipe, or (b) a static pressure due to an acceleration of the particle laden flow in the pipe —12a A signal processor 14 having one or more modules 16 configured to receive signaling containing information about the parameter related to the particle laden flow in the pipe; and determine a measurement of a particle size and either a mass flow rate, or a particle-to-air mass ratio, or both the mass flow rate and the particle-to-air mass ratio, associated with the particle laden flow, based at least partly on a change in the parameter The System

*FIG. 1a*

A Signal Processor 14

One or more modules 16 configured to receive signaling containing information about the parameter related to the particle laden flow in the pipe; and determine a measurement of a particle size and either a mass flow rate, or a particle-to-air mass ratio, or both the mass flow rate and the particle-to-air mass ratio, associated with the particle laden flow, based at least partly on a change in the parameter One or more other modules 18 configured to implement other functionality in relation to signal processing, including input/output, random access memory, read only memory, busing, etc.

The Signal Processor

Possible Implementation of Mass Flow and Particle Size Meter for Particle Laden Flow

APPLICATIONS FOR REAL-TIME MASS RATIO, MASS FLOW AND PARTICLE SIZE MEASUREMENT OF PARTICLE LADEN FLOWS

CROSS-REFERENCE TO RELATED APPLICATIONS

This application claims benefit to international patent application serial no. PCT/US2010/022737, filed 1 Feb. 2010, which claims benefit to provisional patent application Ser. No. 61/148,475 (WFVA/CCS nos. 712-2.315//0011P), filed 30 Jan. 2009; and Ser. No. 61/153,131 (WFVA/CCS nos. 712-2.317//0003P), filed 17 Feb. 2009, which are all incorporated by reference in their entirety.

BACKGROUND OF THE INVENTION

1. Field of Invention

This invention relates to monitoring a particle laden flow in a pipe.

More particularly, this invention relates to a technique for determining real-time particle-to-air mass ratio, mass flow and particle size of particle laden flows in a pipe based at least partly on a change in some parameter related to a particle laden flow, including, e.g., either a sound level propagating through a particle laden flow in a pipe, or a static pressure due to an acceleration of the particle laden flow in the pipe. The change includes an attenuation in a measured parameter related to the particle laden flow, which can be used to monitoring the particle laden flow in the pipe.

2. Description of Related Art

In certain applications, particle laden flows may be monitored based on measurements related to the particle laden flows.

For example, in one known industrial applications related to a pulverized coal-fired power plant, the mass ratio (or inversely the air-to-fuel ratio, AFR) and particle size have a direct impact on combustion dynamics inside a boiler. The boiler will operate most efficiently and while creating the least amount of undesirable emissions at a given AFR and particle size of the pulverized coal fuel. In addition, monitoring these parameters over time would give an indication of the performance degradation and maintenance requirements for certain equipment, such as the coal pulverizers, riffle boxes and damper valves as a few examples.

In view of the aforementioned, there is a need in industry applications to be able to accurately and effectively measure the real-time particle-to-air mass ratio, mass flow and particle size for particle laden flows.

SUMMARY OF THE INVENTION

The present invention provides new techniques for monitoring particle laden flows in a pipe, that include receiving signalling containing information about a parameter related to a particle laden flow in a pipe, the parameter including either (a) a sound level propagating through the particle laden flow in the pipe, or (b) a static pressure due to an acceleration of the particle laden flow in the pipe; and determining a measurement of a particle size and either a mass flow rate, or a particle-to-air mass ratio, or both the mass flow rate and the particle-to-air mass ratio, associated with the particle laden flow, based at least partly on a change in the parameter, including an attenuation or reduction in the parameter.

Signal Processor

According to some embodiments, the present invention may be implemented in apparatus taking the form of a processor, a signal processor, or a signal processor module comprising one or more modules configured to: receive signalling containing information about a parameter related to a particle laden flow in a pipe, the parameter including either (a) a sound level propagating through the particle laden flow in the pipe, or (b) a static pressure due to an acceleration of the particle laden flow in the pipe; and determine a measurement of a particle size and either a mass flow rate, or a particle-to-air mass ratio, or both the mass flow rate and the particle-to-air mass ratio, associated with the particle laden flow, based at least partly on a change in the parameter. The measurement may be used to monitor the particle laden flow.

System

According to some embodiments, the present invention may be implemented in apparatus taking the form of a system used in relation to a pipe having a particle laden flow, where the system comprises a data gathering module and a signal processor. The data gathering module is configured to respond to the particle laden flow in the pipe, and provide signalling containing information about a parameter related to the particle laden flow, where the parameter include either (a) a sound level propagating through the particle laden flow in the pipe, or (b) a static pressure due to an acceleration of the particle laden flow in the pipe. The signal processor has one or more modules configured to receive the signalling containing information about the parameter related to the particle laden flow and to determine a measurement of a particle size and either a mass flow rate, or a particle-to-air mass ratio, or both the mass flow rate and the particle-to-air mass ratio, associated with the particle laden flow based at least partly on a change in the parameter.

Consistent with that described herein, the system may include the change being based at least partly on an acoustic attenuation coefficient that varies with the frequency of the sound level propagating through the particle laden flow in the pipe; the change being based at least partly on an attenuation of the sound propagated through the particle laden flow in the pipe at different frequencies, including two different frequencies; the one or more modules being configured to determine the particle size based on the change in the acoustic attenuation coefficient; the change being based at least partly on a static pressure change due to an acceleration of the particle laden flow caused by a flow area reduction or a flow direction change in the pipe; the change being associated with a reduction of static pressure of the particle laden flow in two different lengths of the pipe having different cross-sectionals areas; the static pressure being reduced in an extended length of the pipe having a reduced cross-sectional area; or some combination of these features.

Applications Related to Mass Flow and Particle Size Measurement of Particle Laden Flows (CCS-0003)

In applications related to mass flow and particle size measurement of particle laden flows, including a pneumatically conveyed activated carbon powder, the change may be based at least partly on a static pressure change due to the acceleration of the particle laden flow caused by a flow area reduction or a flow direction change in the pipe, where the static pressure is reduced in an extended length of the pipe having a reduced cross-sectional area, or having a turn, e.g., in an elbow. The change may be associated with a reduction of static pressure of the particle laden flow in two different lengths of the pipe having different cross-sectionals areas, including where the static pressure is reduced in an extended length of the pipe having a reduced cross-sectional area. In effect, the "reduction" of static pressure is due to acceleration of the fluid/particle mixture. The point of the present invention is that: a higher mass of solid particles in the flow means higher overall density of the gas/particle mixture flowing through the pipe, which means larger reduction of static pressure as it flows through any area changes or elbows. By measuring both the velocity and change in static pressure the density and thus the mass of the particles can be determined.

The one or more modules may be configured to determine a mixture density of the particle laden flow in the pipe by measuring both a velocity and static pressure change across the reduced cross-sectional area, including where the one or more modules is configured to determine the mass flow of the fluid and the particle size based at least partly on the mixture density, flow velocity and the density of the fluid. The one or more modules may also be configured to determine the mass flow of the fluid and the particle size based at least partly on the density of the fluid and particles for flows where the volume of the fluid is not significantly greater than the volume of particles. The one or more modules may also be configured to determine the particle size by measuring the change in the static pressure in an extended length of the pipe having a reduced cross-sectional area, when a material density of the particles is known.

Applications Related to Real-Time Mass Ratio and Particle Size Measurement of Particle Laden Flows (CCS-0011)

Alternatively, in applications related to real-time mass ratio and particle size measurement of particle laden flows, including in a pulverized coal-fired power plant, the change is based at least partly on an acoustic attenuation coefficient that varies with the frequency of the sound level propagating through the particle laden flow in the pipe, including where the one or more modules is configured to determine the particle size based on the change in the acoustic attenuation coefficient. The change may also be based at least partly on an attenuation of the sound propagated through the particle laden flow in the pipe at different frequencies. The one or more modules may be configured to determine the particle size based on the change in the acoustic attenuation coefficient, including where the one or more modules is configured to determine the particle-to-air mass ratio based on the particle size and an absolute value of the acoustic attenuation coefficients, and where the one or more modules is configured to determine a mass flow rate based on the particle-to-air mass ratio and an air velocity as determined by a velocity meter, including a sonar velocity meter. The one or more modules may also be configured to measure the acoustic attenuation coefficient at multiple frequencies, and to determine the particle size and the particle-to-air mass ratio simultaneously by fitting measured data to an analytical model using an optimization routine, including a least squares fit. The date gathering module may also be configured with a sound source and measurement of sound levels at at least two locations, including where the sound source has existing equipment arranged in relation to the pipe, including a fan, a blower, an orifice plate or a coal pulverizer. The data gathering module may also be configured to provide corresponding signalling containing information about the measurement.

The Method

According to some embodiments, the present invention may be implemented in a method comprising: receiving signalling containing information about a change in either (a) a sound level propagating through a particle laden flow in a pipe, or (b) a static pressure due to an acceleration of the particle laden flow in the pipe; and determining a measurement of a particle size and either a mass flow rate, or a particle-to-air mass ratio, or both the mass flow rate and the particle-to-air mass ratio, associated with the particle laden flow based at least partly on the information contained in the signalling received.

The method may also be implemented using one or more of the features set forth above in relation to the processor or system.

Computer-Readable Storage Medium

According to some embodiments, the present invention may be implemented in apparatus taking the form of a computer-readable storage medium having computer-executable components for performing the steps of the aforementioned method.

Alternative Signal Processor Embodiment

According to some embodiments, the present invention may be implemented in apparatus taking the form of a processor, a signal processor, or a signal processor module comprising one or more modules configured to: receive signalling containing information about a parameter related to a particle laden flow in a pipe, the parameter including either (a) a sound level propagating through the particle laden flow in the pipe, or (b) a static pressure due to an acceleration of the particle laden flow in the pipe; and determine a measurement of a particle size and either a mass flow rate, or a particle-to-air mass ratio, or both the mass flow rate and the particle-to-air mass ratio, associated with the particle laden flow being based at least partly on an attenuation or reduction of the parameter, where the attenuation or reduction is related to either the sound level propagating through the particle laden flow in the pipe, or to the static pressure due to the acceleration of the particle laden flow in the pipe, consistent with that described herein.

Advantages of the Present Invention

One advantage of the present invention is that it provides a new way to accurately and effectively measure the real-time particle-to-air mass ratio, mass flow and particle size for particle laden flows, which is needed in industry applications to monitor certain particle laden flows.

BRIEF DESCRIPTION OF THE DRAWING

The drawing includes FIGS. 1-9, which are not drawn to scale, as follows.

DETAILED DESCRIPTION OF BEST MODE OF THE INVENTION

Figure 1A:
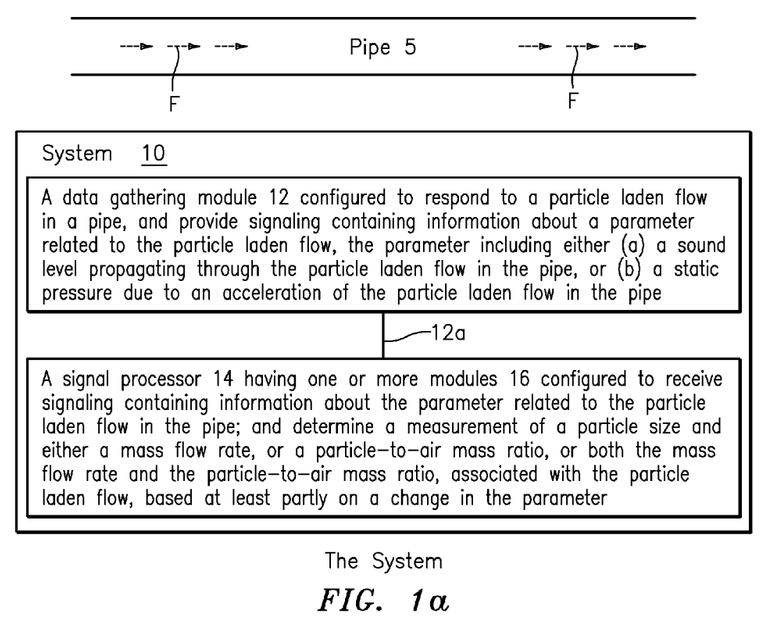
FIG. 1a is a block diagram showing a system according to some embodiment of the present invention.
Figure 1B:
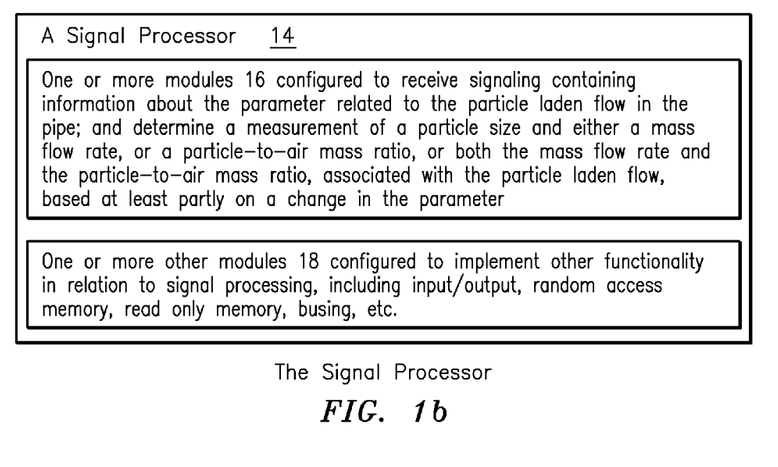
FIG. 1b is a block diagram showing a signal processor that forms part of the system shown in FIG. 1a according to some embodiment of the present invention.

FIG. 1: The Basic Invention

FIG. 1 shows a pipe 5 arranged is relation to a system 10 for monitoring a particle laden flow indicated by arrows labeled F flowing in the pipe 5. The system 10 includes a data gathering module 12 and a signal processor 14, which may also be referred to herein as signal processor, a processor or a signal processor module.

The data gathering module 12 is configured to respond to the particle laden flow F in the pipe 5, and provide signalling along line 12a containing information about a parameter related to the particle laden flow. The parameter may include either (a) a sound level propagating through the particle laden flow in the pipe 5, or (b) a static pressure due to an acceleration of the particle laden flow in the pipe, consistent with that described herein.

The signal processor 14 has one or more modules 16 (see also FIG. 1b) configured to receive the signalling containing information about the parameter related to the particle laden flow and to determine a measurement of a particle size and either a mass flow rate, or a particle-to-air mass ratio, or both the mass flow rate and the particle-to-air mass ratio, associated with the particle laden flow based at least partly on a change in the parameter.

The signal processor 14 is shown in further detail in FIG. 1(b) and may also includes one or more other modules 18 configured to implement other functionality in relation to signal processing, including, but not limited to, input/output, random access memory, read only memory, busing etc. The functionality of the one or more modules 16 of the signal processor 14 may be implemented using hardware, software, firmware, or a combination thereof. In a typical software implementation, the processor modules would include one or more microprocessor-based architectures having a microprocessor, a random access memory (RAM), a read only memory (ROM), input/output devices and control, data and address buses connecting the same. A person skilled in the art would be able to program such a microprocessor-based implementation to perform the functionality described herein without undue experimentation. The scope of the invention is not intended to be limited to any particular implementation using technology either now known or later developed in the future.

The system 10 will be described in further detail below in relation to mass flow and particle size measurement of particle-laden flows, as well as real-time mass ratio and particle size measurement of particle laden flows. However, the scope of the invention is intended to include other embodiments related to other applications for monitoring a particle laden flow in a pipe either now known or later developed in the future.

Mass Flow and Particle Size Measurement of Particle-Laden Flows (CCS-0003)

Figure 2A:
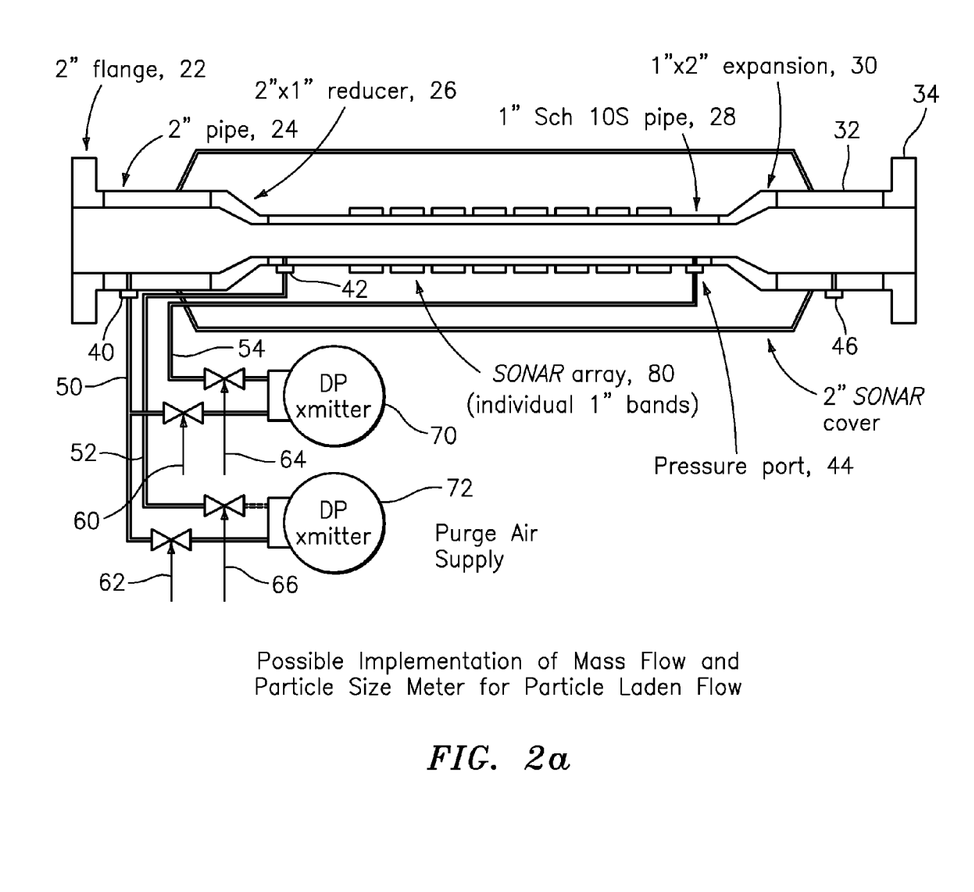
FIG. 2a is a diagram showing a possible implementation for measuring the mass flow and particle size meter for particle laden flows according to some embodiment of the present invention.
Figure 2B:
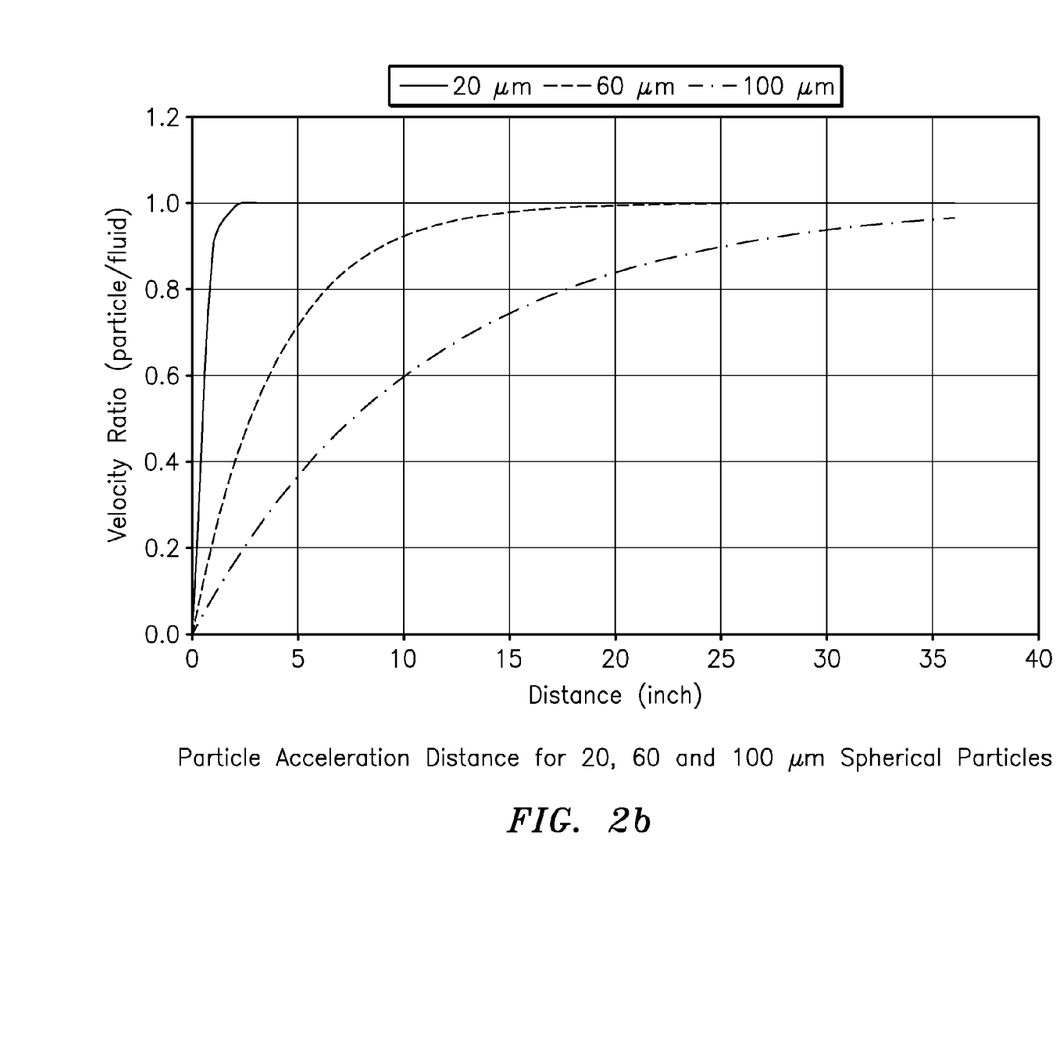
FIG. 2b is a graph of distance (inches) versus velocity ratio (particle/fluid) showing particle acceleration distance for 20 µm, 60 µm and 100 µm sized spherical particles according to some embodiment of the present invention.

FIGS. 2a and 2b show an implementation of the present invention in relation to measuring both the mass flow rate and nominal particle size of particle-laden flows, e.g. a pneumatically conveyed activated carbon powder.

FIG. 2a shows the data gathering module 12 in the form of a pipe reduction section 20 and associated sensing technology arranged in relation thereto. The pipe reduction section 20 forms part of the pipe 5 shown in FIG. 1a. As shown, and by way of example, the pipe reduction section 20 may include a first 2" flange 22, a first 2" pipe 24, a 2"×1" reducer 26, 1" sch 10S pipe 28, a 1"×2" expansion 30, a second 2" pipe 32 and a second 2" flange 34. The scope of the invention is not intended to be limited to the dimensions of these parts, which are provided by way of example. As shown, and by way of example, the associated sensing technology arranged in the pipe reduction section 20 may include pressure ports 40, 42, 44, 46; lines 50, 52, 54; valves 60, 62, 64, 66; a two differential pressure (DP) transmitters 70, 72; and an array of sensor bands 80. The lines 50, 52, 54 and devices 60, 62, 64, 66 combine to couple the pressure ports 40, 42, 44, 46 to the DP transmitters 70, 72. In operation, this associated sensing technology shown in FIG. 2a is configured to respond to the particle laden flow F in the pipe reduction section 20, and provide the signalling along line 12a in FIG. 1a containing information about the parameter related to the particle laden flow. In this case, the parameter includes the static pressure due to the acceleration of the particle laden flow in the pipe reduction section 20, consistent with that described herein.

In operation, when the particle-laden fluid flows through the pipe reduction section 20 having an area reduction as shown in FIG. 2a, the fluid velocity will accelerate in proportion to the ratio of the areas of the pipe 5 (FIG. 1a) and the pipe 28 of the pipe reduction section 20. The particles will also accelerate, but due to inertial force will have a time lag in the acceleration. The magnitude of the time lag is mostly dependant on the density and viscosity of the fluid, and the mass, shape, and surface roughness of the particle.

Due to conservation of energy, a change in static pressure will also occur due to acceleration of the flow caused by the flow area reduction. As the flow accelerates through the area reduction, the static pressure will decrease proportional to the square of the velocity increase. The magnitude of pressure decrease is dependant on the velocity change and the mixture density, which will be sensed by the associated sensing technology, and provided in the signalling along line 12a containing information about the parameter related to the particle laden flow.

The one or more modules 16 of the signal processor 14 receives the signalling along line 12a. In operation, by measuring both the velocity and the static pressure change across the area reduction, the mixture density can be determined by the one or more modules 16. Knowing the mixture density, flow velocity and density of the fluid and particles (or just the fluid density for flows where the volume of the fluid is significantly greater than the volume of the particles), the mass flow of both the fluid and, generally more importantly, the particles can be determined by the one or more modules 16.

The time lag of acceleration of the particles as described above can be used by the one or more modules 16 to determine some other properties of the particles. Specifically, when the material density of the particles is known, the nominal particle size can be determined by the one or more modules 16 by measuring the change in pressure through an extended length of the reduced area section of pipe. The graph in FIG. 2b shows the ratio of the particle velocity to the fluid velocity for three different sized spherical particles. Note that the bigger the particles the longer it takes for the particle velocity (and therefore the static pressure) to fully accelerate.

The associated sensing technology is known in the art, and the scope of the invention is not intended to be limited to any particular type or kind thereof either now known or later developed in the future. By way of example, the associated sensing technology is disclosed in whole or in part, in U.S. Pat. Nos. 7,165,464; 7,134,320; 7,363,800; 7,367,240; and 7,343,820, which are all incorporated by reference in their entirety. The sensing technology disclosed in these cited patents may also be referred to herein as SONAR sensing technology, which was developed be the assignee of the present invention.

Alternatively, the change may be based at least partly on a static pressure change due to the acceleration of the particle laden flow caused by a flow direction change in the pipe. For example, in a turn in the pipe, e.g. in an elbow (see FIG. 3, element 92b) or a fuel nozzle (not shown), the particle laden flow can experience a particle acceleration, e.g. on one side of the pipe during the flow direction change. For example, at a turn in the pipe, the part of the particle laden flow on the inside portion of the elbow may be flowing at one velocity, while another part of the particle laden flow on the outside portion of the elbow may accelerate and be flowing at a faster velocity, causing a pressure decrease in the particle laden flow. As a person skilled in the art would appreciate in these particle laden flows (i.e. air and pulverized coal particles) the density of the coal is over 1000 times that of the air. Therefore, in the case of an elbow the air will easily turn around the elbow but the coal particles will want to keep going in a straight line. The particles will hit the wall of the elbow and momentarily come to a stop. The flow will then have to reaccelerate the particles in the 90 degree direction (assuming a 90 degree elbow of course). This reacceleration will cause a higher static pressure drop between the inlet and outlet of the elbow than if there were no particles present. In other words, the amount of static pressure drop will be approximately proportional to the mass of the particles. Consistent with that described above, the magnitude of the static pressure decrease or reduction is dependant on the velocity change and the mixture density, which will be sensed by the associated sensing technology and provided in the signalling along line 12a containing information about the parameter related to the particle laden flow.

Real-Time Mass Ratio and Particle Size
Measurement of Particle Laden Flows (CCS-0011)

FIGS. 3 through 9 show an implementation of the present invention in relation to measuring real-time mass ratio and particle size measurement of particle laden flows using acoustic attenuation characteristics of these flows, e.g. in a pulzerized coal-fired power plant.

By way of example, the attenuation of propagating acoustic waves is well understood and several models are known in the art. One such attenuation model is given by Gibson and Toksoz in a paper titled "Viscous Attenuation of Acoustic Waves in Suspensions" (Gibson model). In this paper, an analytic derivation of the so-called attenuation coefficient, $\alpha$, in units of decibels per meter is given. The attenuation coefficient describes how the acoustic or sound intensity at a given frequency is reduced as it propagates through the particulate flow.

The Gibson model shows that the acoustic attenuation coefficient varies with frequency. Also the ratio of the acoustic attenuation at two different frequencies is only slightly dependent on the AFR but varies strongly with the particle size. Thus, by measuring the attenuation at two different frequencies using the data gathering module 12 (FIG. 1a), the one or more modules 16 (FIGS. 1a, 1b) can calculate the ratio of the two and determine the particle size. Then, knowing the particle size, the absolute value of the attenuation is used to infer the AFR. Finally, knowing AFR and an air velocity as determined by a velocity meter, including a sonar velocity meter, the mass flow rate of the coal and air is determined by the one or more modules 16 (FIGS. 1a, 1b).

Figure 3:
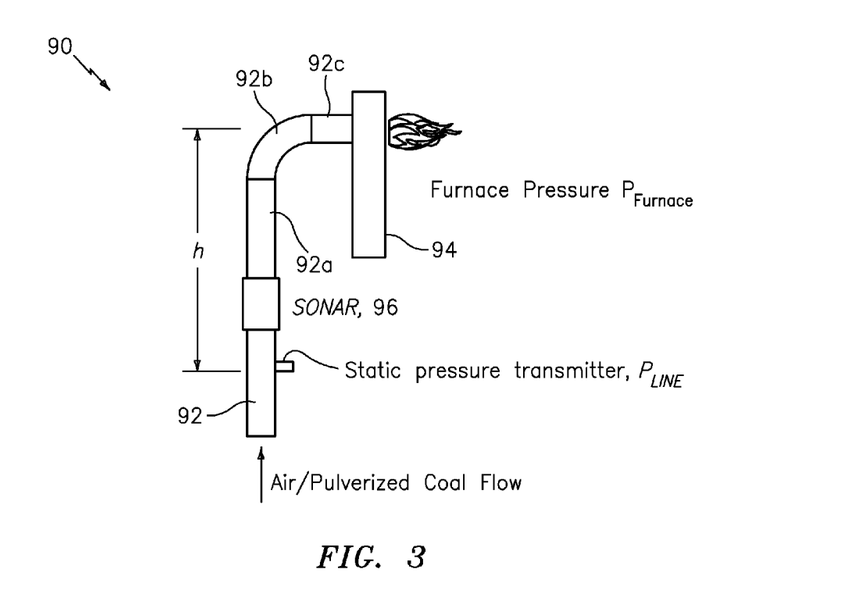
FIG. 3 is a diagram showing a possible implementation for measuring real-time mass ratio and particle size measurement of particle laden flows using acoustic attenuation characteristics of these flows according to some embodiment of the present invention.

FIG. 3 shows a typical installation generally indicated as 90 on a single pipe 92 in relation to a furnace 94. A static pressure transmitter, $P_{Line}$, and a data gathering module 96 in the form of sensing technology described above are arranged in relation to the pipe 92. The pipe 92 includes a first straight pipe portion 92a, an elbow pipe portion 92b and a second straight pipe portion 92c.

The acoustic attenuation coefficient can also be measured at multiple frequencies using the data gathering module 12 (FIG. 1a). It is then possible to determine by the one or more modules 16 (FIGS. 1a, 1b) the particle size and AFR simultaneously by fitting the measured data to the analytical model using an optimization routine such as a least squares fit.

By way of example, the data gathering module 12 (FIG. 1a) may be configured with a sound source and measurement of sound levels at least two locations for measuring the acoustic attenuation. The sound source can be from existing equipment in process (i.e. fan, blower, orifice plate, coal pulverizer, etc.) or an auxiliary sound source specifically for the measurement could be added. By way of example, the acoustic attenuation may at least partly be based on a measured loss in dB/meter. The data gather module signal processor 14 may be configured with hardware, software, firmware, or a combination thereof for implemented the functionality of this embodiment of the system 10 set forth herein, including functionality related to providing signalling for provisioning and/or sensing the sound level propagating through the particle laden flow in the pipe 5 (FIG. 1*a*). In a typical software implementation, the processor modules would include one or more microprocessor-based architectures having a microprocessor, a random access memory (RAM), a read only memory (ROM), input/output devices and control, data and address buses connecting the same. A person skilled in the art would be able to program such a microprocessor-based implementation to perform the functionality described herein without undue experimentation. The scope of the invention is not intended to be limited to any particular implementation using technology either now known or later developed in the future. Adding a sound source would most likely be the best method since it would be consistent.

Factors of importance for this embodiment of the system 10 are as follows:

1. Choice of the measurement frequency range: When calculating the attenuation ratio, using two frequencies that are too close together will result in attenuation ratios that could be difficult to discern. An upper frequency that is too high may result in too low sound levels, a lower frequency too low may result in the attenuation ratio that has an undesirably strong dependence on AFR. If fitting multiple frequency points to the attenuation model, the frequency range must be appropriately selected.

2. The effect of pipe size on the attenuation: Ideally only the attenuation of the fundamental acoustic wave is measured as multi-mode effects are difficult to predict or control. This sets an upper limit for the high frequency range.

3. Location and characteristics of the sound source: The sound source must be strong enough at the chosen frequencies to create measurable attenuation solely due to propagating waves. The source must be at a fixed, well defined position in the pipe.

4. The absolute value of the attenuation: The distance between sound source and acoustic sensors, the distance between acoustic sensors as well as the chosen measurement frequencies must be such that the amount of attenuation is neither too low nor too high.

Each of these factors is described separately below.

Measurement Frequency Range

Figure 4A:
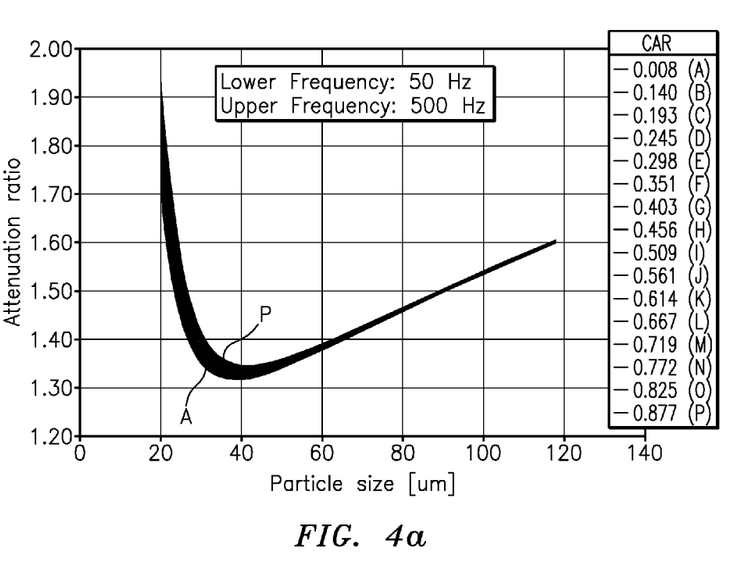
FIG. 4a is a graph of an attenuation ratio plot showing particle size (μm) versus attenuation ratio for various coal-to-air (CAR) ratios in a range of 0.088 to 0.877 for lower and upper frequencies in a range of 50-500 Hz according to some embodiment of the present invention.

FIG. 4*a* shows a graph with results for a number of choices of the upper and lower frequency when calculating the ratio of attenuation coefficient. As the frequency of the upper and lower are increased, the minimum in the attenuation ratio shifts down to lower particle sizes, as shown in FIG. 3*a*.

Figure 4B:
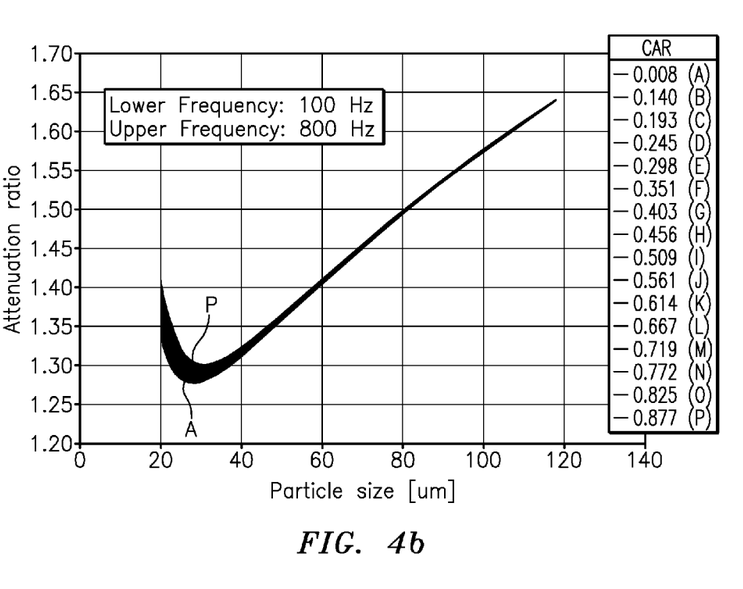
FIG. 4b is a graph of an attenuation ratio plot showing particle size (μm) versus attenuation ratio for various coal-to-air (CAR) ratios in a range of 0.088 to 0.877 for lower and upper frequencies in a range of 100-500 Hz according to some embodiment of the present invention.

FIG. 4*b* shows a graph indicating that, at the same time, with decreasing distance between the upper and lower frequency the absolute difference in the attenuation ratio decreases. Also, using higher frequencies makes the relation between the attenuation ratio and the particle size more non-linear.

Choosing a lower frequency of 100 Hz and an upper frequency of 800 Hz provides for a measurement range in terms of particle sizes from about 40 μm to well over 100 μm. Over this range of particle sizes, the attenuation ratio varies from about 1.3 to more than 1.6 which is about a 20% change. Assuming Sound Power Levels (SPL) of about 100 dB, with a measurable change in attenuation of 1 dB, a 1 dB SPL resolution equates to 1% relative resolution. With an approximate linear relation between the attenuation ratio and the particle size this results in a particle size resolution of about 5 μm.

Pipe Size Effect

The cut-off frequency for multi-mode propagation of acoustical waves in a circular pipe is given by:

$$f_c = \frac{j_{10}c}{2\pi R} = 0.5861 \frac{c}{2R},$$

where $j_{10}$ is the first zero of the derivative of the Bessel function $J_1$, and c is the speed of sound in the medium whereas R is the pipe radius. Table 1 below gives the cut off frequencies for pipes commonly found in coal fired power plants.

TABLE 1

| Diameter | | Speed of sound | Cutoff frequency |
|---|---|---|---|
| inch | mm | m/s | Hz |
| 8 | 203 | 300 | 865 |
| 10 | 254 | 300 | 692 |
| 12 | 305 | 300 | 577 |
| 14 | 356 | 300 | 494 |
| 16 | 406 | 300 | 433 |
| 18 | 457 | 300 | 385 |
| 20 | 508 | 300 | 346 |
| 22 | 559 | 300 | 315 |

Figure 4C:
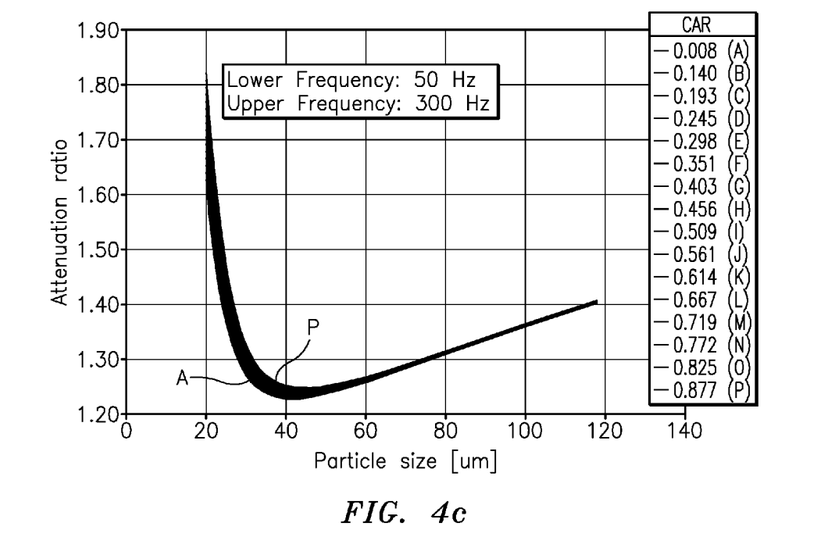
FIG. 4c is a graph of an attenuation ratio plot for a 22" pipe system showing particle size (μm) versus attenuation ratio for various coal-to-air (CAR) ratios in a range of 0.088 to 0.877 for lower and upper frequencies in a range of 50-300 Hz according to some embodiment of the present invention.

Larger pipes limit the useable frequency range as it is important to prevent multi-mode attenuation. For instance, FIG. 4*c* shows a graph of an attenuation ratio plot with a 22" pipe system and with maximum frequency of 300 Hz.

Source of Sound

Figure 5A:
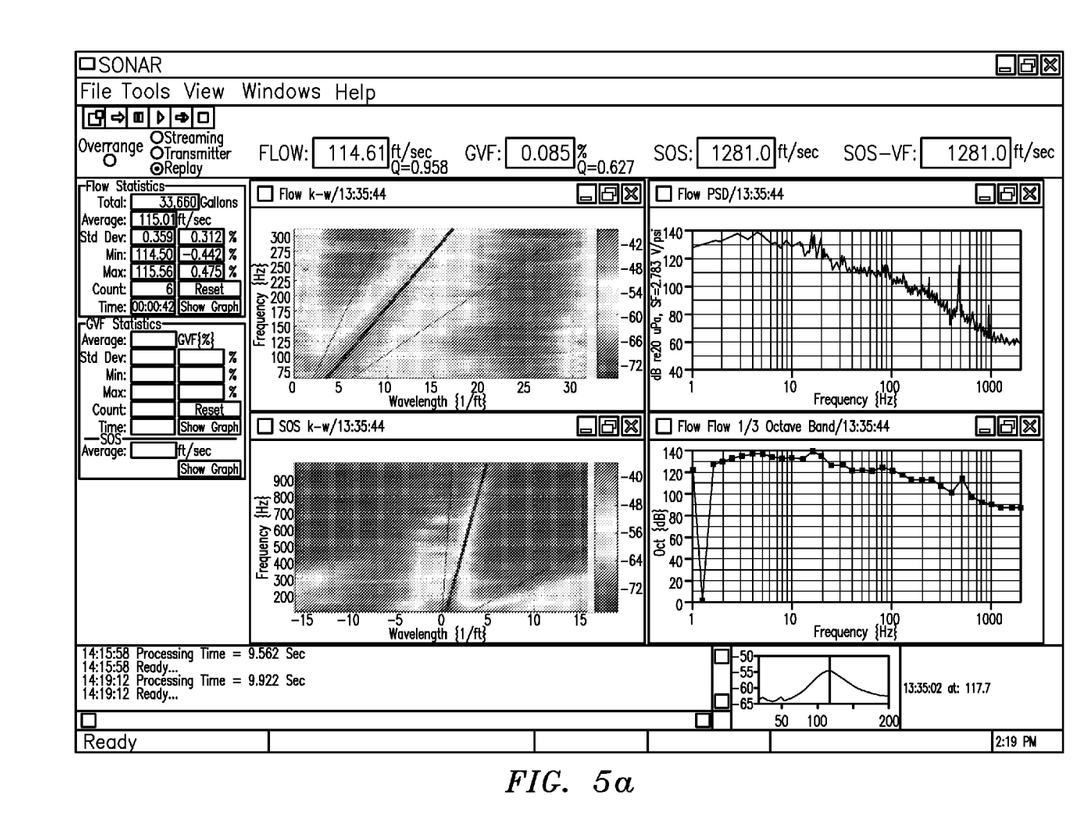
FIG. 5a is a screenshot of time series reprocessing of EPRI coal flow loop data for a CAR of about 0.3 according to some embodiment of the present invention.
Figure 5B:
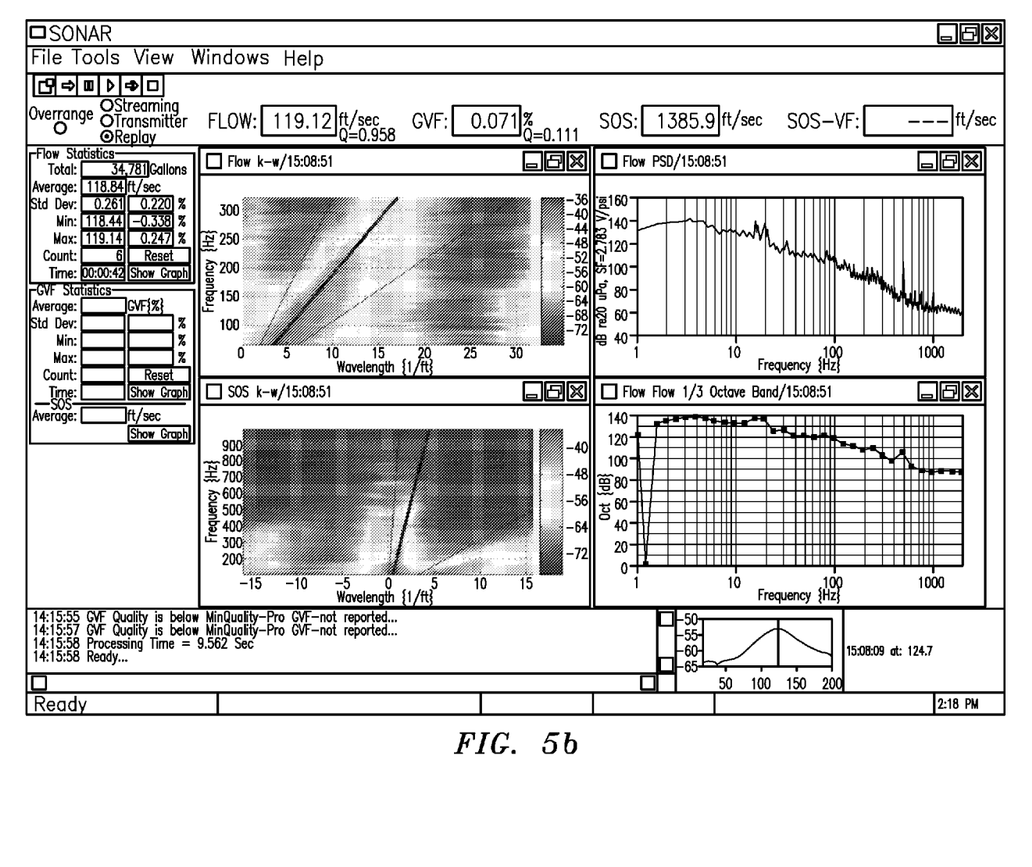
FIG. 5b is a screenshot of time series reprocessing of EPRI coal flow loop data for a CAR of about 0.6 according to some embodiment of the present invention.

The source of sound must produce sound at two or more frequencies. The power output of the source at those frequencies must be high enough to create measurable sound peaks well above the baseline power as generated by the plant's equipment. A screenshot of time series reprocessing of EPRI coal flow loop data gives the values at two different AFR values. FIG. 5*a* shows a shot at a coal-to-air ratio (CAR=1/AFR) of about 0.3, and FIG. 5*b* shows a second at a CAR of about 0.6.

As shown, the power in the ⅓ octave band around 500 Hz decreased by about 7 dB (a factor of 5) by increasing the CAR from 0.3 to 0.6, doubling the CAR resulting in decreasing the coherent sound power by a factor of 5. This sound power at 500 Hz is coherent as evidenced by the blob on the frequency vs. wave number plot.

Figure 6:
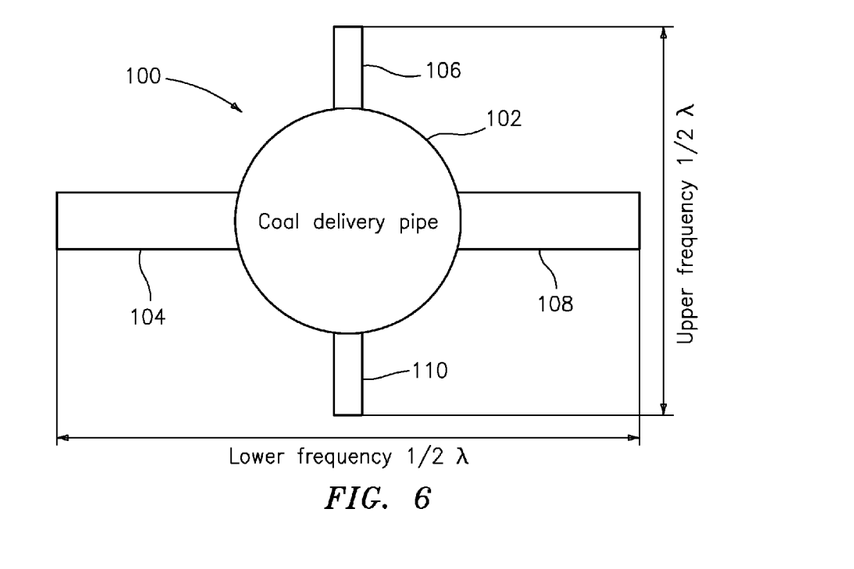
FIG. 6 is a diagram showing an aero-acoustic source consisting of a side branch cross T system with an lower frequency of ½λ and an upper frequency of ½λ according to some embodiment of the present invention.

One potential high power source of sound is an aero-acoustic source consisting of a side branch cross T system generally indicated 100 arranged in relation to a coal delivery pipe 102 as shown in FIG. 6, where the length of side arms 104, 106, 108, 110 fixes the frequency and the diameter of the pipe 102 influences the power output. As shown, the side branch cross T system 100 has an lower frequency of ½λ and an upper frequency of ½λ.

In operation, this type of source uses the vortex shedding at the pipe wall to "T" branch intersection to generate waves. The side branches operate as an organ pipe with two closed ends which forces the system to produce sound of a frequency given by the speed of sound in the medium divided by the wavelength. The wavelength follows as two times the total length of the side branch as at both ends a velocity anti-node (a pressure node) is imposed. Such aero-acoustic sources can produce sound power levels well above 120 dB provided that the flow velocity in the main pipe is high enough.

Attenuation Level and Distance Between Sensors

Figure 7A:
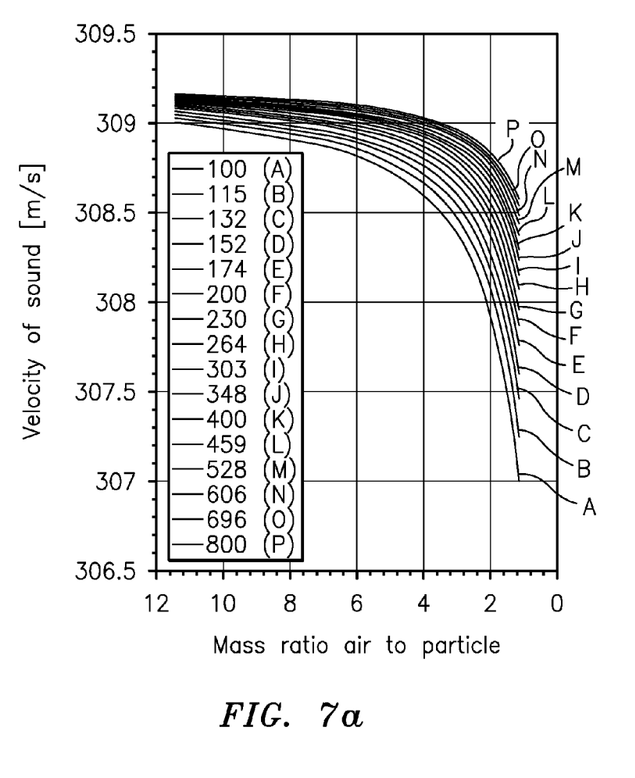
FIG. 7a is a graph of an attenuation ratio plot showing maximum ratio air to particle versus velocity of sound (m/s) for frequencies in a range of 100-800 Hz according to some embodiment of the present invention.
Figure 7B:
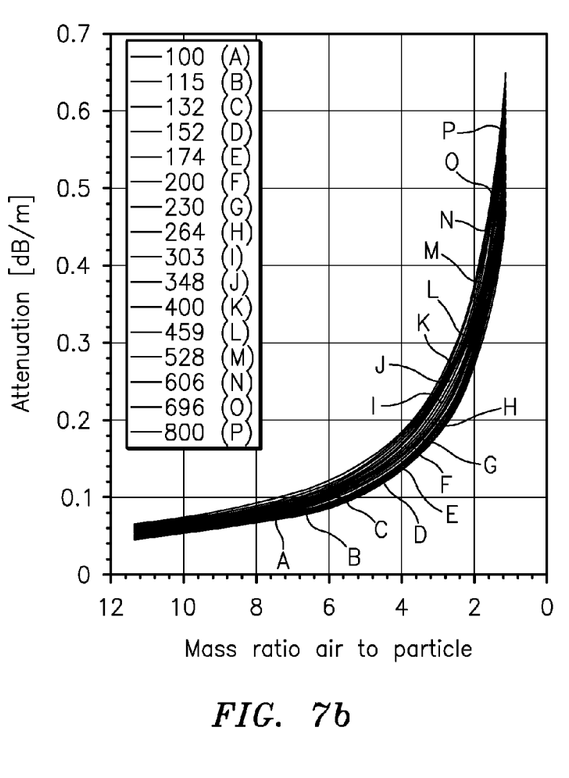
FIG. 7b is a graph of an attenuation ratio plot showing maximum ratio air to particle versus attenuation (dB/m) for frequencies in a range of 100-800 Hz according to some embodiment of the present invention.

The absolute value of the attenuation determines the distance between the sensors. FIGS. 7a, 7b show a graph of an attenuation plot for 50 um particles with frequencies ranging from 100 Hz to 800 Hz.

Figure 8A:
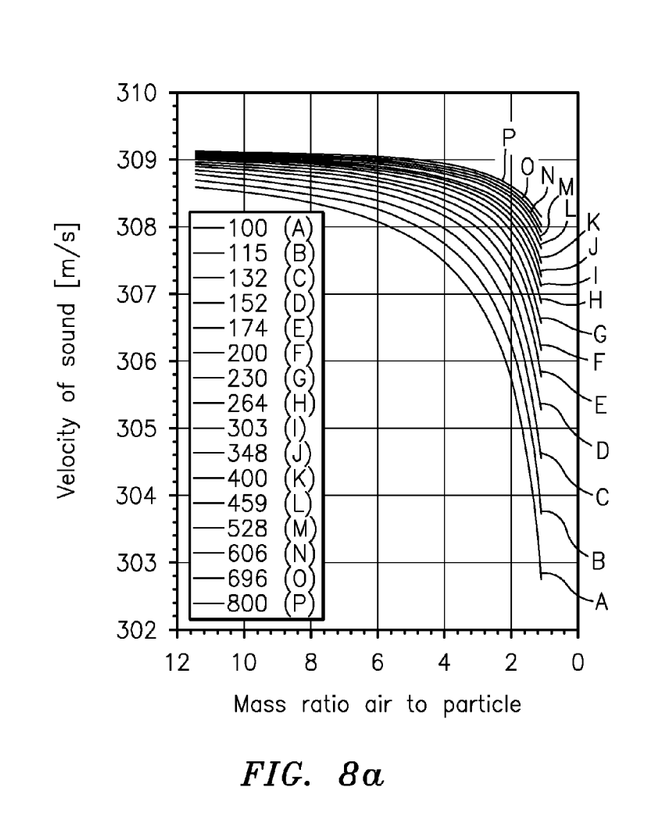
FIG. 8a is a graph of an attenuation ratio plot for 30 μm particles showing maximum ratio air to particle versus velocity of sound (m/s) for frequencies in a range of 100-800 Hz according to some embodiment of the present invention.
Figure 8B:
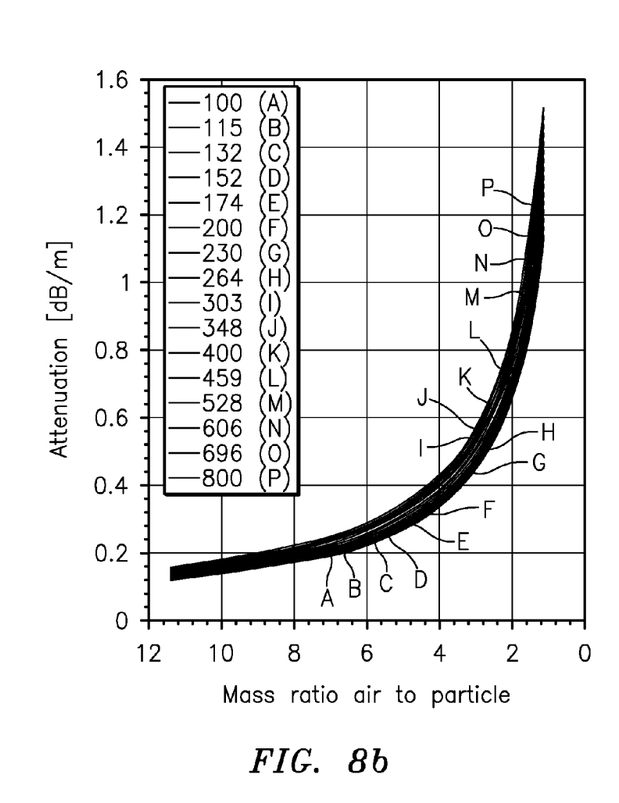
FIG. 8b is a graph of an attenuation ratio plot for 30 μm particles showing maximum ratio air to particle versus attenuation (dB/m) for frequencies in a range of 100-800 Hz according to some embodiment of the present invention.

Attenuation levels are on the order of 0.1 dB/m to 0.5 dB/m. Thus the length required between the acoustic sources must be set so that appreciable attenuation is measured. Doubling or tripling this distance (possibly around bends as bends do not add extra attenuation) is certainly advantageous. Smaller particles will attenuate more, where FIG. 8a, 8b show graphs of attenuation plots for the attenuation of 30 um particles.

Example of Measurements

The measurement of air and coal mass flow rates in pulverized coal pipe systems of coal-fired power plants is important in assuring optimum boiler operation. The measurement can have equal importance in other gas/particle flows as well. The following describes, by way of example, a method of measuring these parameters using data sensing technology, e.g. by combining a clamp-on velocity meter 96 (such as the SONAR technology described above) and a static pressure gauge $P_{Line}$ on the pipe 92, as shown in FIG. 3.

For a given piping system flowing a coal/air mixture the pressure loss through a section of the pipe 92 is a function of an elevation change (h) shown in FIG. 3, a bulk velocity (u), a mixture density (ρ) and the pressure loss coefficient (K):

$$\Delta P = \rho g h + K \frac{1}{2} \rho u^2, \quad (1)$$

where ΔP is the pressure loss and g is the gravity constant. The mixture density is the density of the coal/air mixture flowing through the pipe 92:

$$\rho = \phi_{AIR} \rho_{AIR} + \phi_{COAL} \rho_{COAL}, \quad (2)$$

where φ is the volume fraction of each component. For coal/air mixtures flowing in boiler fuel lines in coal-fired power plants it can be shown that $\phi_{COAL} \ll \phi_{AIR}$ and therefore:

$$\rho = \rho_{AIR} \cdot (1 + CAR), \quad (3)$$

where CAR is the coal/air mass ratio:

$$CAR = \frac{\dot{m}_{COAL}}{\dot{m}_{AIR}}, \quad (4)$$

where m is the mass flow rates of the coal and air. Combining Equations (1) and (3) yields an equation for the coal/air mass ratio:

$$CAR = \frac{\Delta P}{\rho_{AIR} g h + K \frac{1}{2} \rho_{AIR} u^2} - 1. \quad (5)$$

ΔP is the pressure difference between two points in the pipe system. In the case of the pulverized coal burner fuel line, ΔP is measured between the static pressure of the pipe near the location of the meter 96 and the furnace pressure:

$$\Delta P = P_{LINE} - P_{FURNACE}. \quad (6)$$

The pressure loss coefficient is determined through in situ calibration. For single phase flows, i.e. air only, the pressure loss coefficient is a function of only the pipe system geometry (number of elbows, straight run length, wall roughness, etc.). For coal/air mixtures the pressure loss coefficient will also be dependant on the geometry but may also have a slight dependence on coal loading as well. It can be assumed that the pressure loss coefficient is linear with coal/air ratio:

$$K = K_0 + K_1 \cdot CAR, \quad (7)$$

where $K_0$ is the pressure loss coefficient when flowing air only and $K_1$ is the dependence on the CAR. A higher order model could also be incorporated if necessary. Calibration can be performed by operating at a known coal/air ratio, measuring ΔP and velocity, and rearranging equation (5) to solve for K:

$$K = \frac{\frac{\Delta P}{\rho_{AIR}(1 + CAR)} - gh}{\frac{1}{2} u^2}. \quad (8)$$

Figure 9:
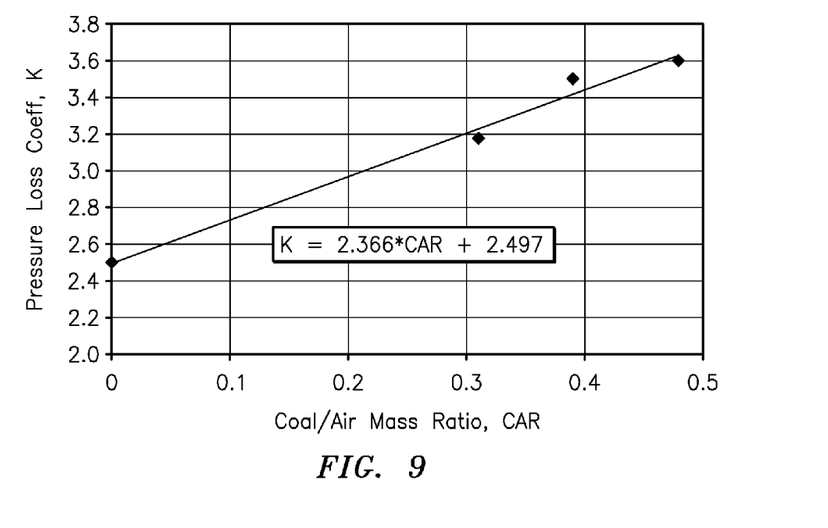
FIG. 9 is a graph of a typical calibration curve showing a coal/air mass ratio (CAR) versus a pressure loss coefficient, K, according to some embodiment of the present invention.

A minimum of two CAR points are required to define the linear relationship of equation (7). Clean air operation (CAR=0) and a typical load setting would be sufficient. Additional load settings could also be used to improve the measurement accuracy. At each calibration point (except clean air) a sampling probe is used to determine the actual CAR. An example of a typical calibration curve is shown in FIG. 9.

The DPDX plus SONAR measurement offers several benefits:
1. It does not require any external inputs such as the pulverizer feed rate. The measurement can then be used to detect feeder abnormalities for example.
2. Functions independent of upstream variable geometry/control components allowing potential for closed loop control
3. It can be installed on an individual pipe if desired, not necessary to instrument the entire pulverizer.
4. It can be completely independent of roping effects since the AP measurement is made over a fairly long pipe section.

THE SCOPE OF THE INVENTION

While the invention has been described with reference to an exemplary embodiment, it will be understood by those skilled in the art that various changes may be made and equivalents may be substituted for elements thereof without departing from the scope of the invention. In addition, modifications may be made to adapt a particular situation or material to the teachings of the invention without departing from the essential scope thereof. Therefore, it is intended that the invention not be limited to the particular embodiment(s) disclosed herein as the best mode contemplated for carrying out this invention.

What is claimed is:
1. A signal processor comprising:
one or more modules configured to:

receive signalling containing information about a parameter related to a particle laden flow in a pipe, the parameter including either (a) a sound level propagating through the particle laden flow in the pipe, or (b) a static pressure due to an acceleration of the particle laden flow in the pipe; and determine a measurement of a particle size and either a mass flow rate, or a particle-to-air mass ratio, or both the mass flow rate and the particle-to-air mass ratio, associated with the particle laden flow, based at least partly on a change in the parameter.

2. A signal processor according to claim 1, wherein the change is based at least partly on an acoustic attenuation coefficient that varies with the frequency of the sound level propagating through the particle laden flow in the pipe.

3. A signal processor according to claim 1, wherein the change is based at least partly on an attenuation of the sound propagated through the particle laden flow in the pipe at different frequencies, including two different frequencies.

4. A signal processor according to claim 2, wherein the one or more modules is configured to determine the particle size based on the change in the acoustic attenuation coefficient.

5. A signal processor according to claim 4, wherein the one or more modules is configured to determine the particle-to-air mass ratio based on the particle size and an absolute value of the acoustic attenuation coefficient.

6. A signal processor according to claim 5, wherein the one or more modules is configured to determine a mass flow rate based on the particle-to-air mass ratio and an air velocity as determined by a velocity meter, including a sonar velocity meter.

7. A signal processor according to claim 2, wherein the one or more modules is configured to measure the acoustic attenuation coefficient at multiple frequencies, and to determine the particle size and the particle-to-air mass ratio simultaneously by fitting measured data to an analytical model using an optimization routine, including a least squares fit.

8. A signal processor according to claim 1, wherein the one or more modules is configured to receive the signalling from a sound source and a measurement device of sound levels arranged at at least two locations on the pipe.

9. A signal processor according to claim 8, wherein the sound source includes existing equipment arranged in relation to the pipe, including a fan, a blower, an orifice plate or a coal pulverizer.

10. A signal processor according to claim 1, wherein the one or more modules is configured to provide corresponding signalling containing information about the measurement for monitoring the particle laden flow in the pipe.

11. A signal processor according to claim 1, wherein the particle laden flow includes air and coal.

12. A signal processor according to claim 1, wherein the change is based at least partly on a static pressure change due to the acceleration of the particle laden flow caused by a flow area reduction or a flow direction change in the pipe.

13. A signal processor according to claim 1, wherein the change is associated with a reduction of static pressure of the particle laden flow in two different lengths of the pipe having different cross-sectionals areas.

14. A signal processor according to claim 12, wherein the static pressure is reduced in an extended length of the pipe having a reduced cross-sectional area.

15. A signal processor according to claim 14, wherein the one or more modules is configured to determine a mixture density of the particle laden flow in the pipe by measuring both a velocity and static pressure change across the reduced cross-sectional area.

16. A signal processor according to claim 15, wherein the one or more modules is configured to determine the mass flow of the fluid and the particle size based at least partly on the mixture density, flow velocity and the density of the fluid.

17. A signal processor according to claim 16, wherein the one or more modules is configured to determine the mass flow of the fluid and the particle size based at least partly on the density of the fluid and particles for flows where the volume of the fluid is not significantly greater than the volume of particles.

18. A signal processor according to claim 1, wherein the one or more modules is configured to determine the particle size by measuring the change in the static pressure in an extended length of the pipe having a reduced cross-sectional area, when a material density of particles in the particle laden flow is known.

19. A signal processor according to claim 1, wherein the particle laden flow in the pipe includes a pneumatically conveyed activated carbon powder.

20. A system configured to be arranged in relation to a pipe providing a particle laden flow, comprising:

a data gathering module configured to respond to the particle laden flow in the pipe, and provide signalling containing information about a parameter related to the particle laden flow, the parameter including either (a) a sound level propagating through the particle laden flow in the pipe, or (b) a static pressure due to an acceleration of the particle laden flow in the pipe; and a signal processor having one or more modules configured to receive the signalling containing information about the parameter related to the particle laden flow, and to determine a measurement of a particle size and either a mass flow rate, or a particle-to-air mass ratio, or both the mass flow rate and the particle-to-air mass ratio, associated with the particle laden flow based at least partly on a change in the parameter.

21. A system according to claim 20, wherein the change is based at least partly on an acoustic attenuation coefficient that varies with the frequency of the sound level propagating through the particle laden flow in the pipe.

22. A system according to claim 20, wherein the change is based at least partly on an attenuation of the sound propagated through the particle laden flow in the pipe at different frequencies, including two different frequencies.

23. A system according to claim 21, wherein the one or more modules is configured to determine the particle size based on the change in the acoustic attenuation coefficient.

24. A system according to claim 20, wherein the change is based at least partly on a static pressure change due to the acceleration of the particle laden flow caused by a flow area reduction or a flow direction change in the pipe.

25. A system according to claim 20, wherein the change is associated with a reduction of static pressure of the particle laden flow in two different lengths of the pipe having different cross-sectionals areas.

26. A system according to claim 20, wherein the static pressure is reduced in an extended length of the pipe having a reduced cross-sectional area, or having a turn in the pipe, including an elbow.

27. A method comprising:

receiving signalling containing information about a parameter related to a particle laden flow in a pipe, the parameter including either (a) a sound level propagating through the particle laden flow in the pipe, or (b) a static pressure due to an acceleration of the particle laden flow in the pipe; and determining a measurement of a particle size and either a mass flow rate, or a particle-to-air mass ratio, or both the mass flow rate and the particle-to-air mass ratio, associated with the particle laden flow, based at least partly on a change in the parameter.

28. A method according to claim 27, wherein the change is based at least partly on an acoustic attenuation coefficient that varies with the frequency of the sound level propagating through the particle laden flow in the pipe.

29. A method according to claim 27, wherein the change is based at least partly on an attenuation of the sound propagated through the particle laden flow in the pipe at different frequencies, including two different frequencies.

30. A method according to claim 28, wherein the method comprises determining the particle size based on the change in the acoustic attenuation coefficient.

31. A method according to claim 27, wherein the change is based at least partly on a static pressure change due to the acceleration of the particle laden flow caused by a flow area reduction in the pipe.

32. A method according to claim 27, wherein the change is associated with a reduction of static pressure of the particle laden flow in two different lengths of the pipe having different cross-sectionals areas, or having a turn in the pipe, including an elbow.

33. A method according to claim 27, wherein the method comprises reducing the static pressure in an extended length of the pipe having a reduced cross-sectional area.

34. A signal processor comprising:
one or more modules configured to:
receive signalling containing information about a parameter related to a particle laden flow in a pipe, the parameter including either (a) a sound level propagating through the particle laden flow in the pipe, or (b) a static pressure due to an acceleration of the particle laden flow in the pipe; and
determine a measurement of a particle size and either a mass flow rate, or a particle-to-air mass ratio, or both the mass flow rate and the particle-to-air mass ratio, associated with the particle laden flow being based at least partly on an attenuation or reduction of the parameter.

35. A signal processor according to claim 34, wherein the attenuation or reduction is related to either the sound level propagating through the particle laden flow in the pipe, or to the static pressure due to the acceleration of the particle laden flow in the pipe.

36. Apparatus comprising:
means for receiving signalling containing information about a parameter related to a particle laden flow in a pipe, the parameter including either (a) a sound level propagating through the particle laden flow in the pipe, or (b) a static pressure due to an acceleration of the particle laden flow in the pipe; and
means for determining a measurement of a particle size and either a mass flow rate, or a particle-to-air mass ratio, or both the mass flow rate and the particle-to-air mass ratio, associated with the particle laden flow, based at least partly on a change in the parameter.

37. Apparatus according to claim 36, wherein the change is based at least partly on an acoustic attenuation coefficient that varies with the frequency of the sound level propagating through the particle laden flow in the pipe.

38. Apparatus according to claim 36, wherein the change is based at least partly on an attenuation of the sound propagated through the particle laden flow in the pipe at different frequencies, including two different frequencies.

39. Apparatus according to claim 37, wherein the particle size is determined based on the change in the acoustic attenuation coefficient.

40. Apparatus according to claim 36, wherein the change is based at least partly on a static pressure change due to the acceleration of the particle laden flow caused by a flow area reduction in the pipe.

41. Apparatus according to claim 36, wherein the change is associated with a reduction of static pressure of the particle laden flow in two different lengths of the pipe having different cross-sectionals areas, or having a turn in the pipe, including an elbow.

42. Apparatus according to claim 36, wherein the static pressure is reduced in an extended length of the pipe having a reduced cross-sectional area.

* * * * *